United States Patent
Gillis et al.

(12)
(10) Patent No.: US 6,468,264 B1
(45) Date of Patent: Oct. 22, 2002

(54) CLOSED EXCHANGE SYSTEM

(75) Inventors: Edward M. Gillis, Cupertino, CA (US); Timothy Scott Nelson, Los Gatos, CA (US)

(73) Assignee: Durect Corporation, Cupertino, CA (US)

(*) Notice: Subject to any disclaimer, the term of this patent is extended or adjusted under 35 U.S.C. 154(b) by 0 days.

(21) Appl. No.: 09/416,588

(22) Filed: Oct. 12, 1999

(51) Int. Cl.[7] .......................... A61K 9/22; A61M 31/00
(52) U.S. Cl. ...................... 604/891.1; 604/513; 604/59
(58) Field of Search ............... 604/891.1, 19, 604/27, 28, 36, 38, 48, 500, 502, 506, 508, 513, 57, 59–64, 93.01, 218, 244, 288.01–288.04, 11, 14, 15–18, 233; 222/135, 138, 139, 144, 145.1, 167, 168, 168.5

(56) References Cited

U.S. PATENT DOCUMENTS

| | | | |
|---|---|---|---|
| 5,354,284 A | * 10/1994 | Haber et al. | 604/191 |
| 5,599,316 A | 2/1997 | Blakely | 604/232 |
| 5,651,767 A | 7/1997 | Schulman et al. | 604/8 |
| 5,728,396 A | 3/1998 | Peery et al. | 424/422 |
| 5,787,900 A | 8/1998 | Butler et al. | 128/898 |
| 5,798,114 A | 8/1998 | Elsberry et al. | 424/423 |
| 5,837,276 A | 11/1998 | Cheikh | 424/423 |
| 6,102,844 A | * 8/2000 | Ravins et al. | 600/7 |
| 6,296,624 B1 | * 10/2001 | Gerber et al. | 604/164.09 |

OTHER PUBLICATIONS

Reynolds, Dwight W., et al., "NASPE Expert Consensus Statement: Physician Workforce in Cardiac Electrophysiology and Pacing," PACE (Aug. 1998) vol. 21:1646–1655.

* cited by examiner

Primary Examiner—Michael J. Hayes
Assistant Examiner—Catherine Serke
(74) Attorney, Agent, or Firm—Pamela J. Sherwood; Bozicevic, Field & Francis LLP (57) ABSTRACT

The invention provides a means of closed exchange of implanted medical device components. An exchanger is brought into contact with the implanted medical device in situ. The component is withdrawn from the implanted device and brought into a closed chamber of the exchanger. Without breaking the contact between implanted device and exchanger, the replacement component is then moved from its position in the exchanger, and inserted into the correct position in the implanted device. The surfaces of the implanted device are not brought into contact with the outside environment, thereby minimizing the possibility of introducing contaminants into the body during the exchange process. The invention is particularly useful for devices that are difficult to position and re-position, thus making it advantageous to exchange only an expended component, rather than the entire device.

24 Claims, 8 Drawing Sheets

CLOSED EXCHANGE SYSTEM

BACKGROUND OF THE INVENTION

Modern technology has allowed the manufacture and use of many medically useful implanted devices. A big advantage to these devices is that there is a continuous contact with physiological fluids and tissues. This contact allows monitors to maintain a constant vigilance on key physiological parameters; pacemakers to correct rhythmic irregularities; and drug delivery implants to keep constant levels of pharmaceutically active compounds in the bloodstream. Implanted devices may also serve structural functions, such replacement hip joints, vascular stents, etc.

Drug delivery implants provide a solution to a number of problems associated with bolus delivery of pharmaceutical agents. Few therapeutic regimen involve administration of a single dose of a selected drug. Instead, most therapies require administration of multiple doses. Where the therapy requires parenteral delivery of the drug, the patient can be subjected to the substantial discomfort and inconvenience of repeated injections. Typically, parenteral drug delivery also requires administration of a bolus of drug in order to provide for an effective drug concentration at the desired treatment site and/or to provide for an adequate systemic levels for an acceptable period of time. Delivery of a drug bolus not only requires delivery of a greater amount of drug, thus driving up the cost of therapy, but can also be associated with undesirable side effects.

One approach for avoiding at least some of the problems inherent in long-term drug delivery involves the use of an implantable drug delivery device. Examples of such implantable drug delivery devices include implantable diffusion systems (see, e.g., subdermal implants (such as NORPLANT#) and other such systems. Alternatively, the implant may be based upon an osmotically-driven device to accomplish controlled drug delivery (see, e.g., U.S. Pat. Nos. 3,987,790, 4,865,845, 5,057,318, 5,059,423, 5,112,614, 5,137,727, 5,234,692; 5,234,693; and 5,728,396). These osmotic pumps generally operate by imbibing fluid from the outside environment and releasing corresponding amounts of the therapeutic agent.

A disadvantage of implanted devices in general is that there is a risk of infection when the device is introduced. Care must be taken during insertion to maintain a clean environment, so that potentially pathogenic microorganisms are not introduced into the body. When delivering drugs to specific sites within the body, it may be desirable to do so through a permanently and fully implanted pump and catheter system. Having the system fully implanted can minimize potential risk of infection because the entire system is located under the skin, minimizing contact with the external environment. Today, the reservoirs of such pump systems are refilled by introducing a needle across the skin and through a silicone septum, and into the drug reservoir of the pump, introducing a possible contaminant pathway to the dry reservoir.

Rather than refilling a reservoir via an external needle, it may be desirable to change out the entire drug reservoir within the body. To minimize the risk of contamination, it is desirable to make this exchange through a closed system. Further, other medical device components, such as batteries in pacemakers, or monitoring cartridges, may also benefit from a closed exchange exchange. The development of such methods would provide a substantial medical benefit.

RELEVANT LITERATURE

An implantable drug delivery device is described by Peery et al., U.S. Pat. No. 5,728,396, issued Mar. 17, 1998. Fluid from the environment in imbibed through a semipermeable plug into the water-swellable agent chamber, and the active agent formulation is released through a back diffusion regulating outlet.

U.S. Pat. No. 5,787,900 describes a method and apparatus for loading and reloading a therapeutic drug in an implantable apparatus. The device is further described in U.S. Pat. No. 5,843,069. Refillable drug delivery techniques are described in U.S. Pat. No. 5,798,114.

An apparatus for the delivery of elongated solid drug compositions is described in U.S. Pat. No. 5,837,276. A portable drug delivery system is described in U.S. Pat. No. 5,599,316. A replaceable catheter system is described in U.S. Pat. No. 5,651,767.

Pacemakers and other implantable cardiac devices are well known in the art. For example, see Reynolds et al. (1998) Pacing Clin Electrophysiol 21(8):1646–55, NASPE expert consensus statement: physician workforce in cardiac electrophysiology and pacing. NASPE task force, Washington, D.C.

An in vivo method for repairing a ruptured segment of an implanted device is described by Hogan, et al, U.S. Pat. No. 5,653,759. A guiding catheter and deformable, thermoelastic shape-memory alloy rods are used to access and repair the flawed or failing therapeutic appliance in place.

Replaceable batteries for implantable medical devices are described by Mulier, U.S. Pat. No. 5,314,451. The circuitry for an electromedical device is contained in a hermetic enclosure, while a power supply for the device is contained in a second hermetic enclosure. The two enclosures are coupled together via a multiple conductor lead, which allows replacement of depleted batteries without explanation of the medical device itself. U.S. Pat. No. 4,294,891 provides an intermittently refuelable implantable biooxidant fuel cell. Refueling occurs by injection.

SUMMARY OF THE INVENTION

The present invention provides a device and method for the closed exchange of a component in an implanted medical device. The exchanger is brought into contact with the implanted medical device in situ. The component is withdrawn from the implanted device and brought into a chamber of the exchanger. Without breaking the contact between implanted device and exchanger, the replacement component is then moved from its position in the exchanger,. and inserted into the correct position in the implanted device. Components of interest for exchange include drug delivery cartridges, e.g. where an expended cartridge is replaced with a loaded cartridge. Also of interest are components such as pacemaker batteries, monitoring devices, and the like.

In one aspect the exchanger features a multi-chambered barrel capable of holding at least one replacement component. After the old component is withdrawn from the implanted device, the barrel is rotated such that the replacement component is brought into position for insertion. The exchanger is optionally provided with a preloaded replacement component.

In another aspect, the exchanger features a multi-chambered barrel, where the replacement component and the expended component are angled to each other, such that each can be inserted or withdrawn through a central contact point without rotation.

In yet another aspect, the invention features a system for maintaining delivery of a drug to a treatment site, where a drug delivery element is a component of the system. The present methods and exchanger provide a means of closed exchange for the drug delivery device component. The implanted device may comprise a flexible guide comprising a proximal end, a distal end, a guide body, and a stable positioning element, where the guide body defines a lumen extending from the guide proximal end to the guide distal end. A drug delivery device is removably and stably positioned within the guide lumen. The drug delivery device is positioned for delivery of drug from a drug reservoir of the drug delivery device and through the distal end of the guide lumen.

A primary object of the invention is to provide a means of closed exchange of implanted device components. An important advantage of the invention is that the internal surfaces of the implanted device are not brought into contact with the outside environment, where contamination and infection may occur. The invention is particularly useful for devices that are difficult to position and re-position, thus making it advantageous to exchange only the expended component, rather than the entire device.

These and other objects, advantages and features of the present invention will become apparent to those skilled in the art upon reading this disclosure in combination with drawings wherein like numerals refer to like components throughout.

DETAILED DESCRIPTION OF THE PREFERRED EMBODIMENTS

Before the present closed exchange system, method of component exchange, and specific devices used in connection with such are described, it is to be understood that this invention is not limited to the particular embodiments described, as such methods, devices, and formulations may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural referents unless the context clearly dictates otherwise. Thus, for example, reference to "a formulation" includes mixtures of different formulations, and reference to "the method of delivery" includes reference to equivalent steps and methods known to those skilled in the art, and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the specific methods and/or materials in connection with which the publications are cited.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

Closed exchange system: refers to a system where the exchange of a component in an implanted medical device takes place in a substantially contained space that is not exposed to the external environment. The interior of the implanted device is not brought into contact with the outside environment.

Implantable devices encompass, but are not necessarily limited to, devices that can be substantially completely implanted within the body of a subject. For example, an "implantable" device that is substantially completely implantable is one that is implanted at a subcutaneous site and, in some embodiments, extends to a site distal to the subcutaneous site (e.g., to a treatment site located deeper within the subject's body, such as the spinal cord).

Component is used to refer to an implantable device or an element that is a part of an implantable device, and will frequently refer to a component that comprises a depletable resource, e.g. a battery, reagents for metabolite monitoring, a drug reservoir containing pharmaceutically active agents, and the like. The term "expended" may be used herein to refer to the component that is to be replaced; which may be depleted of a resource, or otherwise be desirable to replace.

Such components will preferably be designed for replacement, and may be modified for use with the present invention. Such modifications may include locking/unlocking mechanisms to facilitate release of the expended component, and secure locking in place of the replacement component. The component may also be modified to comprise an attachment element, e.g. a "lip" on the edge of the component to provide a secure attachment with the exchanger for removal.

Controlled release as used herein, e.g. in the context of "controlled drug release" is meant to encompass release of a pharmaceutically active substance, e.g., a drug, at a selected or otherwise controllable rate,. interval, and/or amount.

"Controlled release" thus encompasses, but is not necessarily limited to, substantially continuous delivery, patterned delivery, e.g. intermittent delivery over a period of time that is interrupted by regular or irregular time intervals, and delivery of a bolus of a selected substance, e.g. as a pre-determined, discrete amount of a substance, over a relatively short period of time.

The term "controlled drug release device" is meant to encompass any device that provides for controlled release of a drug or other desired substance and that can be adapted for use in the drug delivery device of the invention, e.g., a drug delivery device that provides for controlled release of drug through a drug delivery catheter associated with the drug reservoir, and at a rate that is suitable to accomplish delivery of a therapeutically effective amount of drug to a treatment site according to the methods of the invention.

The term "access site" or "implantation site" is used to refer to a site on or in a subject at which an implantable device has been introduced for implantation and positioning within the subject's body, e.g., for delivery of drug to a desired treatment site. The implantation site may be distinct from the treatment site. For example, a pacemaker may be implanted subcutaneously but act on cardiac tissue; or a drug delivery device in combination with a guide may be implanted at a subcutaneous site at which a proximal end of the guide is substantially retained, where the treatment site is a position within or adjacent to a targeted tissue, at which a distal end of the guide is positioned for delivery of drug.

The term "subject" is meant any subject, generally a mammal (e.g., human, canine, feline, equine, bovine, etc.), in which the implantable device is implanted.

The term "drug" as used herein is meant to encompass any substance suitable for delivery to a treatment site of a subject, which substances can include pharmaceutically active drugs, as well as biocompatible substances that do not exhibit a pharmaceutical activity in and of themselves, but that provide for a desired effect at a treatment site.

"Pharmaceutically active drug," "therapeutic agent," "therapeutic drug," and the like are used interchangeably herein to refer to any chemical compound which, when provided to a subject, facilitates a therapeutic effect. Such drugs may optionally be provided in combination with pharmaceutically acceptable carriers and/or other additional compositions such as antioxidants, stable positioning agents, permeation enhancers, etc.

The term "therapeutically effective amount" is meant an amount of a therapeutic agent, or a rate of delivery of a therapeutic agent, effective to facilitate a desired therapeutic effect. The precise desired therapeutic effect will vary according to the condition to be treated, the drug to be administered, and a variety of other factors that are appreciated by those of ordinary skill in the art. Determinations of precise dosages are routine and well within the skill in the art.

The term "treatment" is used here to cover any treatment of any disease or condition in a mammal, particularly a human, and includes: a) preventing a disease, condition, or symptom of a disease or condition from occurring in a subject which may be predisposed to the disease but has not yet been diagnosed as having it; b) inhibiting a disease, condition, or symptom of a disease or condition, e.g., arresting its development and/or delaying its onset or manifestation in the patient; and/or c) relieving a disease, condition, or symptom of a disease or condition, e.g., causing regression of the disease and/or its symptoms.

Aseptic, or sterilized, as known in the art, refers to a device or reagent that has been treated in such a way that no viable microorganisms or spores are present. Many methods of sterilization are known and used, including heat, ionizing radiation, exposure to toxic gases, sterile filtration, etc. Once sterilized, the internal surfaces that are sealed from outside exposure will remain sterile. The devices of the present invention may be rendered sterile prior to use. This may be accomplished by separately sterilizing each component, then aseptically assembling the final system. Alternatively, the devices may be assembled, then terminally sterilized using any appropriate method.

Overview of the Invention

The present invention provides an closed exchanger for the replacement of components in implanted medical devices. The exchanger allows a component, for example an expended drug delivery cartridge or battery, to be replaced while maintaining contamination-free conditions in the internal areas of the device.

During operation of the exchanger, the exchanger is brought into contact with the implanted medical device in situ and attached this device, in such a way that the internal surfaces of the device and the exchanger are closed to potential external contamination. The component of interest is withdrawn from the implanted device and brought into a closed chamber of the exchanger. Without breaking the contact between the implanted device and the exchanger, the replacement component is then moved from its position inside the exchanger, and inserted into the correct position in the implanted device.

The exchanger device comprises a contact port, or element, that is brought into contact with the implanted device. The contact port forms a secure seal with the implanted device, such that the internal portions of the device and the exchanger are not open to the external environment. In a preferred embodiment, a single contact port is present on the exchanger.

The contact port attaches through a portal to the proximal end of a closed chamber. The closed chamber, portal and contact port form a continuous open path, of sufficient width to permit passage of the component to be replaced. During the replacement process, the exchanged components are manipulated by a movement element, which allows the components to move through the continuous open path. That is, an expended component can be withdrawn with a movement element through the contact port, to be brought into and enclosed by the closed chamber. The replacement component is similarly brought into position by movement out of the closed chamber, through the contact port and into the implanted device.

The contact port may utilize a variety of structural configurations. In one embodiment, the contact port is a tubular member, including a variety of cross-sectional geometries, and of dimensions sufficient to allow passage of the exchangeable components. An alternative contact port is an O-ring that forms a seal with the implanted device.

In one embodiment of the invention, there is a seal at the portal, which is the point of contact between the closed chamber and the contact element. The seal may be of a diaphragm type, where it is broken by the movement of the exchangeable component in or out of the chamber, or a flat sheet of elastomeric material with a hole punched in it. Alternatively, a tight O-ring seal may be positioned around the opening.

In another embodiment, the chamber that the expended component goes into is initially open, with the replacement component in a closed chamber. The opening of the chamber is rotated around a pivot, to be exposed to the opening and the inside area of the implanted device.

The chamber is an enclosed element, of an appropriate size and shape to hold at least two of the exchangeable components, i.e. one replacement component and one expended component. The two components may be arranged in a parallel fashion, so that they can be moved in and out of the exchanger without interfering with each other. Typically the closed chamber will be shaped to fit the component, where the cross-sectional geometry may be of various shapes, e.g. circular, oval, hexagonal, square, etc. The cross-sectional geometry need not be uniform over the length of the chamber, as illustrated in FIG. 4.

Suitable materials for the exchanger chamber generally comprise a moldable or cast polymer, or a biocompatible metal or alloy. Clear materials may be used in order to view the closed chamber. Suitable polymers include, but are not necessarily limited to, acrylonitrile polymers such as acrylonitrile-butadiene-styrene polymer, and the like; halogenated polymers such as polytetrafluoroethylene, polychlorotrifluoroethylene, copolymer tetrafluoroethylene and hexafluoropropylene; polyimide; polysulfone; polycarbonate; polyethylene; polypropylene; polyvinylchloride-acrylic copolymer; polycarbonate-acrylonitrile-butadiene-styrene; polystyrene; and the like. Further exemplary polymers are described in Plastics Materials, 5$^{th}$ Edition, J. R. Brydsun (1995). Metallic materials include stainless steel, titanium, platinum, tantalum, gold and their alloys; gold-plated ferrous alloys; platinum-plated titanium, stainless steel, tantalum, gold and their alloys as well as other ferrous alloys; cobalt-chromium alloys; and titanium nitride-coated stainless steel, titanium, platinum, tantalum, gold, nickel-titanium, nitinol, and their alloys. Also of interest are glass and modified forms of glass materials, including ceramics, etc.

In one embodiment of the invention, the enclosed chamber will form separate compartments for each of the exchangeable components. For example, the chamber may be formed of a plastic, where it is a solid piece having open compartments to hold each exchangeable component. Alternatively, the compartments are partially enclosed, where the compartment walls are sufficient to hold the component in position for insertion or after withdrawal.

For convenience, in discussing the use of the device, the compartment into which the expended component is withdrawn will be referred to as a "withdrawal" compartment, and the compartment containing the replacement component is referred to as the "insertion" compartment. In some embodiments of the invention, the insertion compartment will be pre-loaded with the replacement component.

Figure 1A:
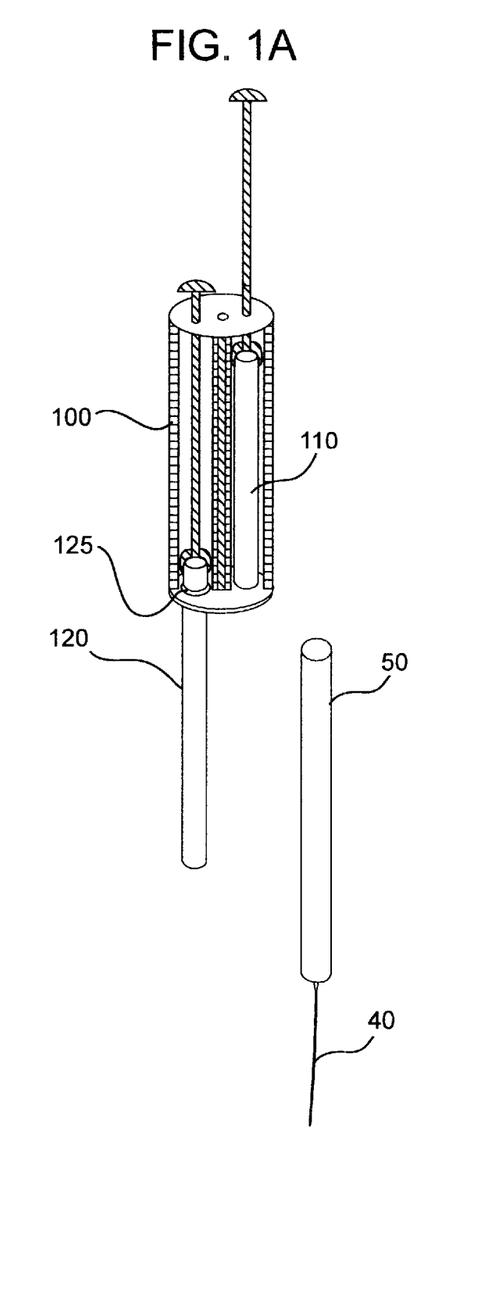
FIG. 1A shows an embodiment of the closed exchanger, used in combination with a drug delivery cartridge. The drug delivery cartridge is shown fitted into an implanted device for sustained release of the drug.
Figure 1B:
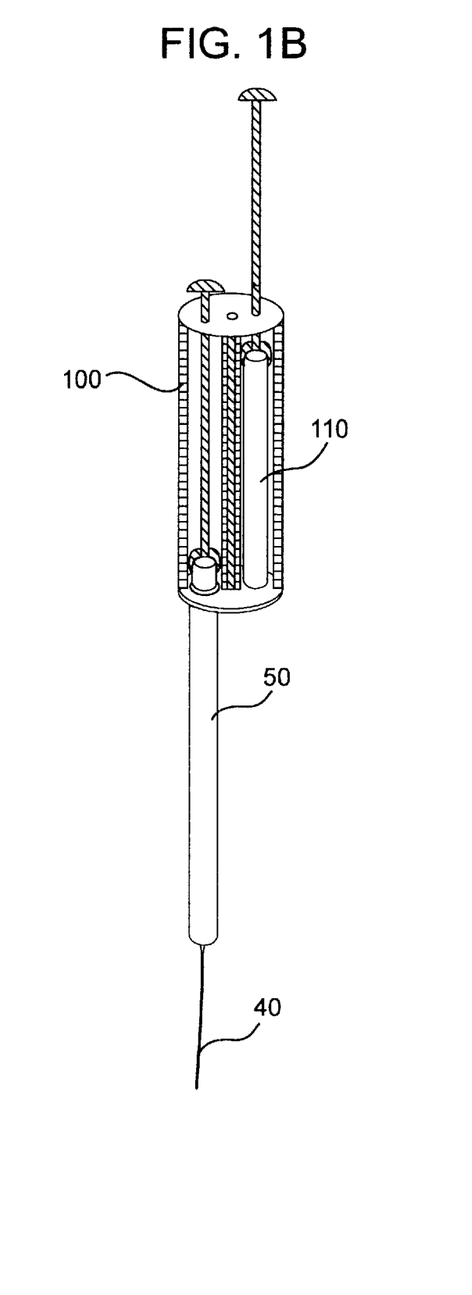
FIG. 1B illustrates the contact between the exchanger and the implanted device.
Figure 1C:
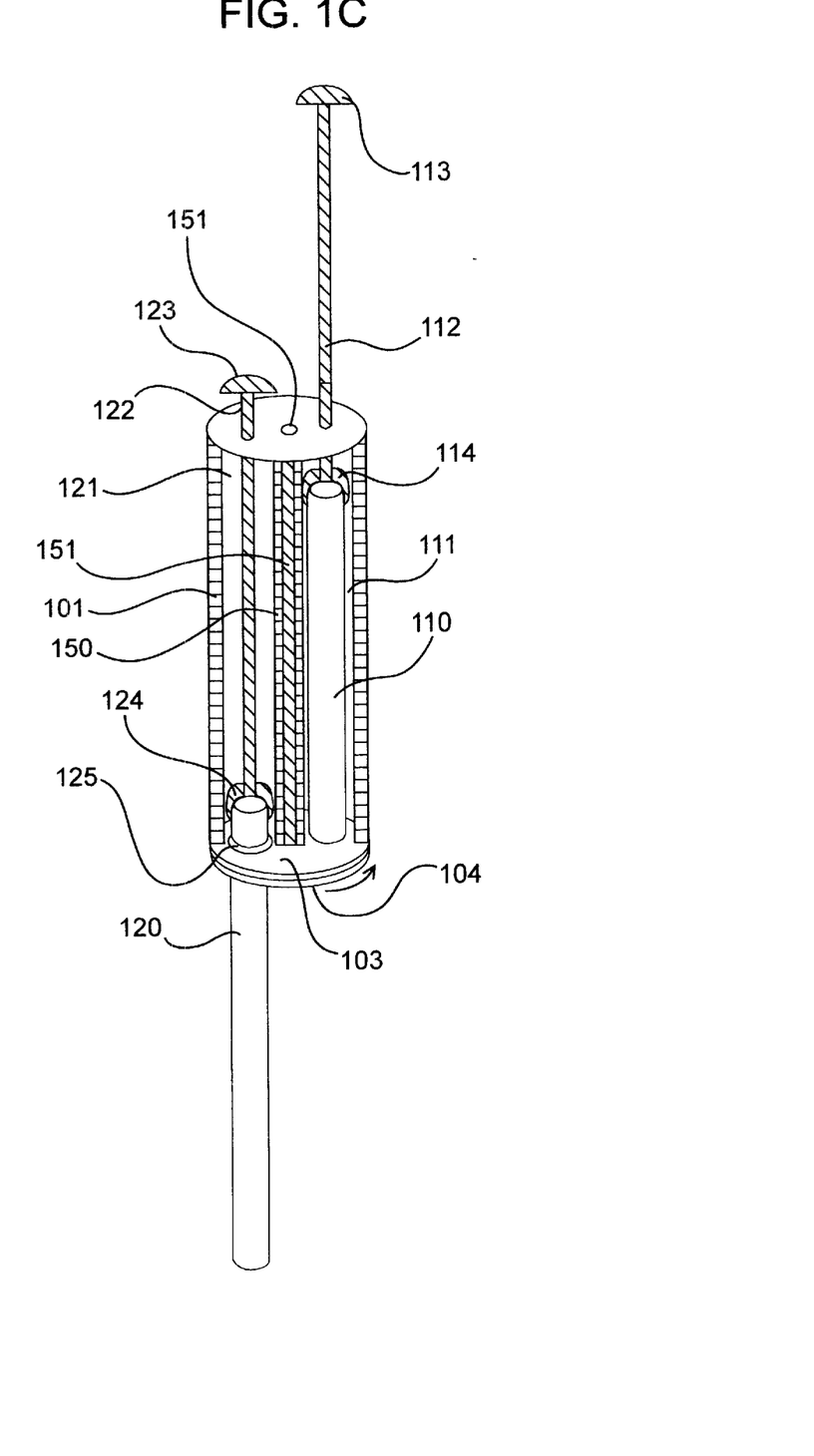
FIG. 1C is a detailed drawing of an exchanger. Alternative embodiments are shown in FIG. 1D, and in FIG. 1E.

In one embodiment of the invention, the closed chamber is formed into a multi-compartmented barrel, where each compartment is capable of holding at least one exchangeable component, shown in FIG. 1C. In this embodiment, two or more elongated compartments are arranged side by side, to be roughly parallel. A similar structure is shown in FIG. 1E, where two squared chambers are situated side by side. Typically, a single contact port and portal are provided, as shown in the figures. The two chambers are rotated about a central axis to bring one of the chambers into alignment with the portal. For example, the contact element may be joined to a disk that is positioned at the bottom of the barrel, and through which the central pivot extends. The barrel is then rotated in relation to the disk. The rotation allows each of the component compartments to be positioned in a continuous access path with the contact element.

Figure 4A:
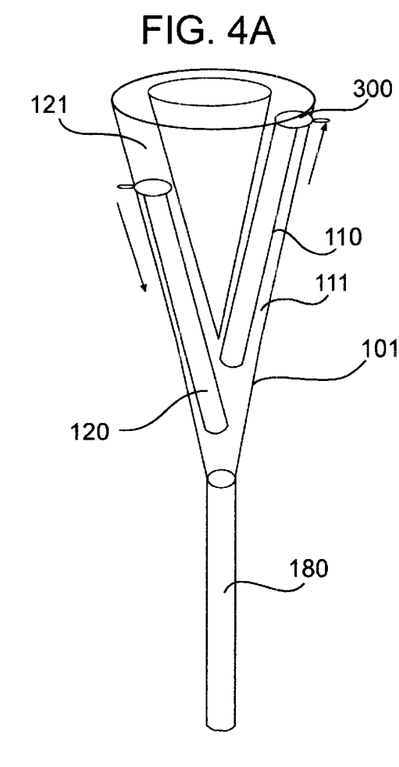
FIGS. 4A and 4B show an embodiment of the closed exchanger, with an angled barrel.

In another embodiment of the invention, the multi-compartmented barrel is roughly funnel-shaped, as shown in FIG. 4A, where each chamber is oriented at an angle, where the angle comes to a point at the contract portal. In this embodiment, a single contact element is joined to the closed chamber at one portal. The access path from the contact port is bifurcated, where the exchangeable component may be moved in or out of an angled compartment.

The top of the closed chamber comprises a small opening above, or to the side, of each of the component compartments, to provide access for the movement element. The opening through which the movement element extends will typically have an O-ring or similar seal, such that there is minimal exposure to the external environment. Usually there will be movement element for each compartment.

The exchange movement device mechanically moves the exchangeable component in or out of the implantable device. In one embodiment of the invention, it is an elongated member that acts as a plunger to translate components in and out of the closed chamber. Such an elongate member will comprise a distal end, which may be a handle, knob, etc., and a proximal end that is brought into contact with the exchangeable component. The exchanger may comprise one or more movement elements. Where there is a single movement element, it may be combined with a rotating barrel in order to position it for use with two or more exchangeable elements.

Figure 6A:
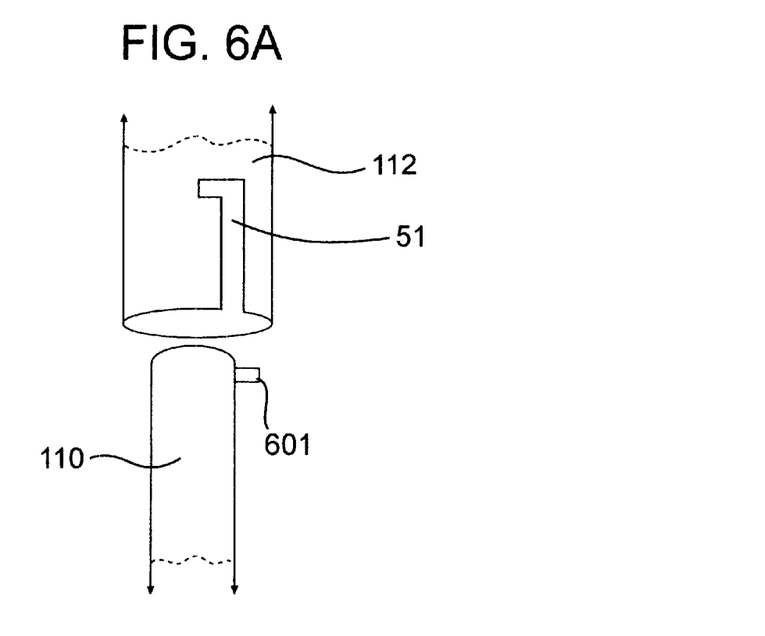
FIG. 6A and FIG. 6B illustrate some locking devices for the exchanger movement element.
Figure 6B:
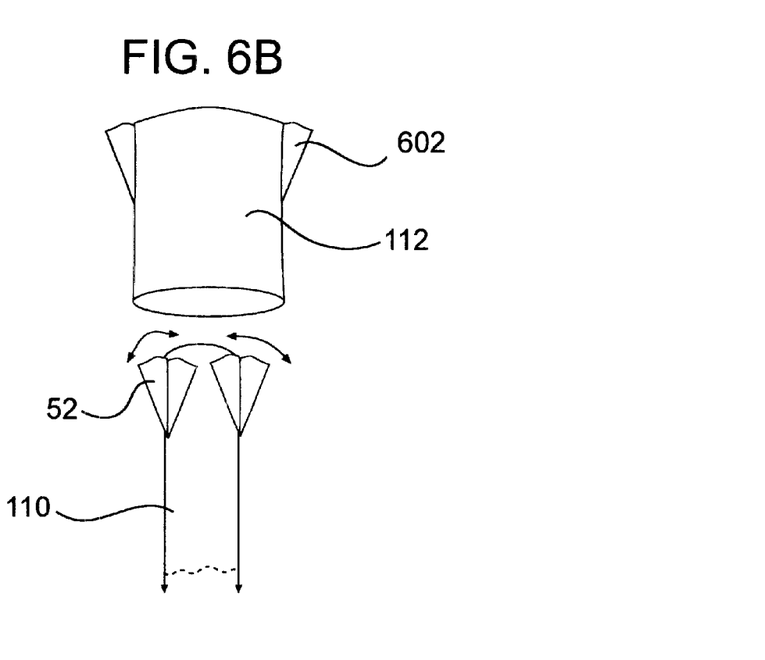

Preferably the movement element is closely coupled to the exchangeable a component for withdrawal or insertion, but the coupling can be broken after insertion is complete. The contact may be of any type that provides sufficient strength to withdraw the component from the implanted device. Such contacts include, for example, various physical means where a lock is formed between the movement element and the component. The component and movement element may be threaded, so that the movement element screws down over the component. Or, the component may have a lip on the outermost surface, over which a flexible flange can be fitted. A small pin may protrude from the component, and a corresponding channel be cut into the movement device, to form a "turn and lock" contact. A releasable "Jaw" may be used, anastomic elements, detent (i.e. a ballplunger), a hex, etc., as are known in the art. Some of these embodiments are depicted in FIGS. 6A and 6B.

In the use of the subject closed exchanger, a component of an implanted medical device is removed and replaced with a new component. The internal surfaces of the implanted device are not brought into contact with the outside environment during this process. The invention is particularly useful for devices that are difficult to position and re-position, thus making it advantageous to exchange only the expended component, rather than the entire device.

The implanted device is accessed through an incision in the skin, made using standard surgical techniques. Removal and/or replacement of the drug delivery device can be accomplished using tools and methods that are readily available. For example, where the implanted device is retained at a subcutaneous site, the component is replaced by first locating the guide proximal end (and/or drug release device proximal end) by fingertip palpation of the subcutaneous site of insertion. After anesthetizing the subject at least locally, an incision is made through the skin and any fibrous capsule tissue surrounding the area of implantation. The end of the device opposite the incision is pushed so that the end of the device is positioned close to, or outside of the incision.

The contact port is brought into contact with the implanted device, and a firm contact is made, in order to minimize the chance of exposing of the implant's inner surfaces to the outside environment. The rotating chamber, when present, is rotated such that there is a continuous access from the implanted device, through the contact port, and into the withdrawal compartment.

The expended component is then contacted with the movement element, for example by pushing down on the movement element and moving it through the contact port, until it touches the expended component. As previously discussed, the movement element will form a locking contact that is sufficiently strong to withdraw the component from the device. The component is extracted, and drawn up into the closed chamber. Generally, the expended component will be within and enclosed by the closed chamber after withdrawal.

In the embodiments of the invention where there is a pivoting, or rotating set of compartments, the compartments are rotated so that the insertion compartment forms a continuous path with the contact element.

The replacement component is then pushed through out of the compartment, through the contact port, and into position in the implanted device by the movement element. The component may be securely fitted into the device by friction, or it may have a locking mechanism, e.g. be threaded into position; have a luer lock, a lock and dock mechanism, and the like.

After insertion of the replacement component, the movement element is withdrawn into the closed chamber, the contact port is released from the implanted device, and the exchanger is removed. Upon completion, the device is then urged back into the original incision, and the incision closed. This procedure can be designed so that removal and replacement of drug delivery devices can be performed on an outpatient basis, and with minimal discomfort to the subject.

In one embodiment of the invention, the exchanger is used to replace a drug delivery component, and the exchanger may be provided pre-loaded with such a component. Drug release cartridges, or components, suitable for use in the present invention may be based on any of a variety of drug delivery systems. For example, the component can be based upon a drug diffusion system, e.g., where the drug is incorporated into a polymer, or the drug could be provided within a drug-impermeable reservoir that is in communication with a drug delivery catheter, particularly where the drug release device is accomplished by a convective drug delivery system, e.g. osmotic pumps, electroosmosis, vapor pressure pumps, electrolytic pumps, effervescent pumps, piezoelectric pumps, etc. Drug release devices based upon a mechanical or electromechanical infusion pump, are also suitable for use with the present invention. Examples of such devices include those described in, for example, U.S. Pat. Nos. 4,692,147; 4,360,019; 4,487,603; 4,360,019; 4,725,852, and the like.

In one embodiment, the drug release device is a controlled drug release device in the form of an osmotically-driven device. Exemplary osmotically-driven devices suitable for use in the invention include, but are not necessarily limited to, those described in U.S. Pat. Nos. 3,760,984; 3,845,770; 3,916,899; 3,923,426; 3,987,790; 3,995,631; 3,916,899; 4,016,880; 4,036,228; 4,111,202; 4,111,203; 4,203,440; 4,203,442; 4,210,139; 4,327,725; 4,627,850; 4,865,845; 5,057,318; 5,059,423; 5,112,614; 5,137,727; 5,234,692; 5,234,693; 5,728,396; and the like.

In one embodiment the controlled drug release device is an osmotic pump, e.g., an osmotic pump similar to that described in U.S. Pat. No. 5,728,396. In one embodiment of particular interest, the osmotic pump is a DUROS™ osmotic pump. In general, osmotic pumps operate by imbibing fluid from the outside environment and releasing corresponding amounts of the therapeutic agent. The reservoirs of osmotic pumps can be a single chamber, or can be divided into two chambers (e.g., a piston can separate the two chambers). Where the pump comprises two chambers, the first chamber (which lies within one portion of the drug release device reservoir) contains a fluid-imbibing agent, and the second chamber (which lies within a second portion of the drug release device reservoir) contains a therapeutic agent. The fluid-imbibing agent in the first chamber is isolated from the active agent in the second chamber. Where a piston serves to separate the two chambers, the piston is capable of sealably moving under pressure within the reservoir. The device may be connected to a "dock" and catheter with access to normally protected sites, for example to bypass the blood brain barrier. In such cases, it is desirable to maintain sterility in the fluid pathway, in order to eliminate potential introduction on infectious agents, e.g. meningitis causing microorganisms.

The following examples are put forth so as to provide those of ordinary skill in the art with a complete disclosure and description of how to make and use the subject invention, and are not intended to limit the scope of what is regarded as the invention. For example, while a drug delivery device is illustrated with the exchanger, other forms and types of controlled components, as well as other forms and variations of implanted devices, are suitable for use in invention.

EXAMPLES

Example 1

Rotating Barrel Exchanger

In one embodiment of the invention, the closed chamber is segregated into two or more compartments, each compartment capable of holding and enclosing an exchangeable component. In order to provide an access pathway through the contact element, the barrel of the closed chamber rotates about a central pivot point. An exchanger of this type is illustrated in FIGS. 1A, 1B and 1C.

FIG. 1A shows an exchanger 100 pre-loaded with a replacement component 110 and in the process of withdrawing an expended component 120. For purposes of illustration only, an exemplary implantable device is shown, comprising a housing 50 and a catheter 40. In this figure, the contact portal is a simple O ring at the portal, 125. For illustration, the housing is shown separate from the expended component. FIG. 1B shows the same exchanger, as it is seen in situ when brought into close contact with the housing 50.

FIG. 1C shows a detailed view of a two-barreled, rotating exchanger. The enclosed chamber of the exchanger 101 has two compartments: a withdrawal compartment 121 and an insertion compartment 111, into which fit the components to be exchanged. It will be readily ascertained by one of skill in the art that the compartments can take on various geometries to fit a variety of components.

Figure 2:
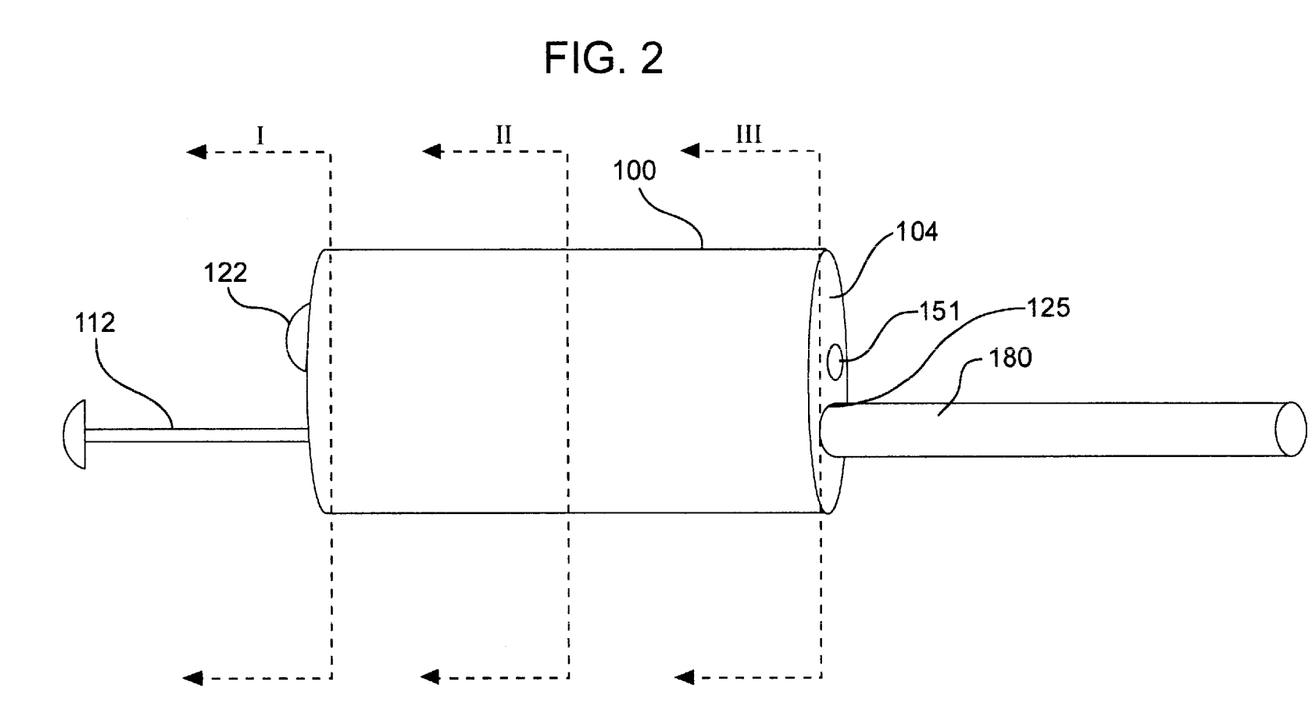
FIG. 2 is an external view of the exchanger, showing a contact port, and showing the placement of cross-sections for FIG. 3.

At the base of the chamber 103, the chamber opens through an aperture 125. The aperture is preferably sealed, with a barrier that maintains sterility within the chamber, which barrier will only be broken during the exchange process itself. The aperture 125 may be positioned so as to form a contiguous access space with a contact port, for example 180 as shown in FIG. 2.

The components are removed and inserted with a movement element 112 or 122, which is shown as an elongated shaft extending through the closed chamber housing. The movement element is capable of firmly attaching to the component at one end for removal, and may further be manipulated to unlock a component featuring a locking system. The movement element may have at one end, attachment element that are designed to attach to the exchangeable component. Shown are one example, of claw shaped attachment elements 124 and 114. Alternative attachment elements are depicted in FIG. 6A and FIG. 6B. The shaft of the movement element, 122 and 112, extend through the barrel of the exchanger, and may have a gripping element 113 and 123 for handling.

The closed chamber rotates about a central pivot 151 which extends through the closed chamber. The chamber is rotated to bring the component compartments 111 and 121 in position with respect to the portal and contact port for exchange. The pivot may be enclosed in a housing 15o to isolate it from the closed compartments.

Figure 1D:
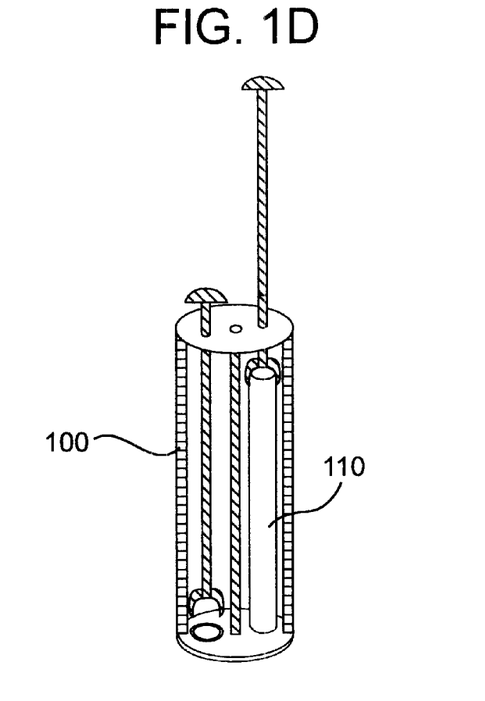
Figure 1E:
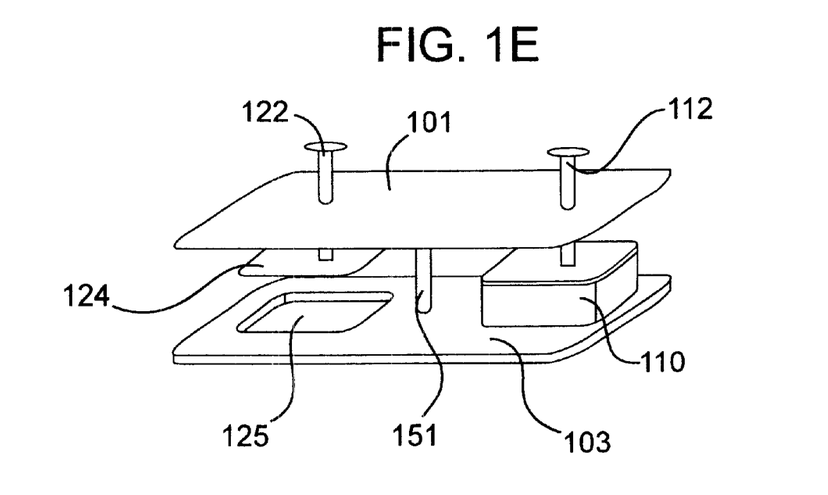

FIG. 1D shows an alternative embodiment of the exchanger 100, where the exchangeable components, e.g. 110, are not fitted into separate chambers.

A similar exchanger structure is shown in FIG. 1E, where two squared exchangeable elements are situated side by side. A central pivot 151 serves as a point of rotation for the exchanger. The exchangeable component 110 is brought into alignment with the portal 125, which extends through the base of the chamber 103. The movement elements 112 and 122 move the exchangeable component through the portal.

The exchanger is also shown in FIG. 2 as an external view, where the exchanger 100 is a closed housing, except for the openings through a portal 125 in the exchanger base 104, and to the movement elements 112 and 122 and pivot 151. The portal leads to a contact port 180. FIG. 2 also shows the position of cross-sections shown in FIGS. 3A, B and C.

Figure 3A:
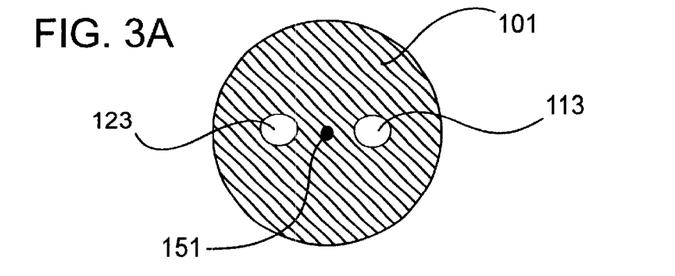
FIG. 3 is a top view cross-section of a rotating barrel exchanger.

A top view cross-section, illustrated in FIG. 3A, shows the top of the chamber casing 101, with the movement elements 113 and 123 and the central pivot 151. The cross-section of FIG. 3B shoes the position of two exchangeable elements, 120 and 110, with a central pivot 151 and optional casing 150.

Figure 3B:
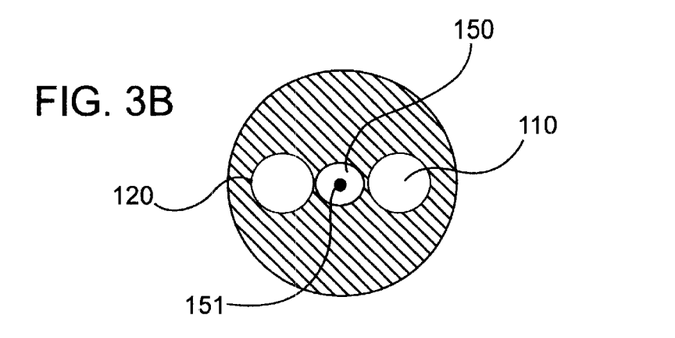
FIG. 3B is a cross-section of a rotating barrel exchanger.
Figure 3C:
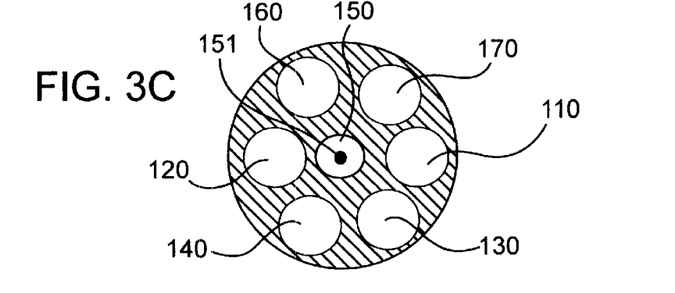
FIG. 3C is another cross-section of a rotating barrel exchanger.

An alternative embodiment is shown in FIG. 3C, which is the same cross section as FIG. 3B. This section shows a closed chamber with multiple exchangeable elements, 110, 120, 130, 140, 160, 170.

Figure 3D:
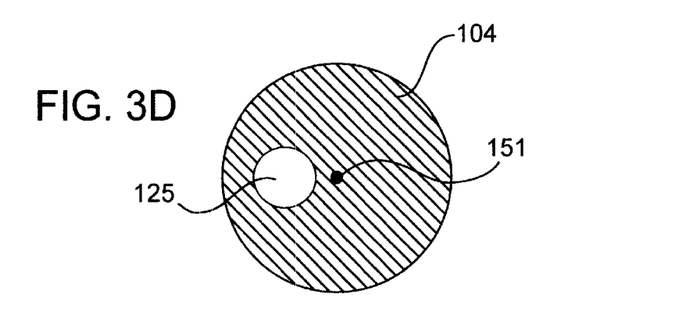
FIG. 3D is a bottom view cross-section of a rotating barrel exchanger.

FIG. 3D is a cross-section at the base of the exchanger 104, through which extend the pivot 151 and the access portal 125.

Figure 5A:
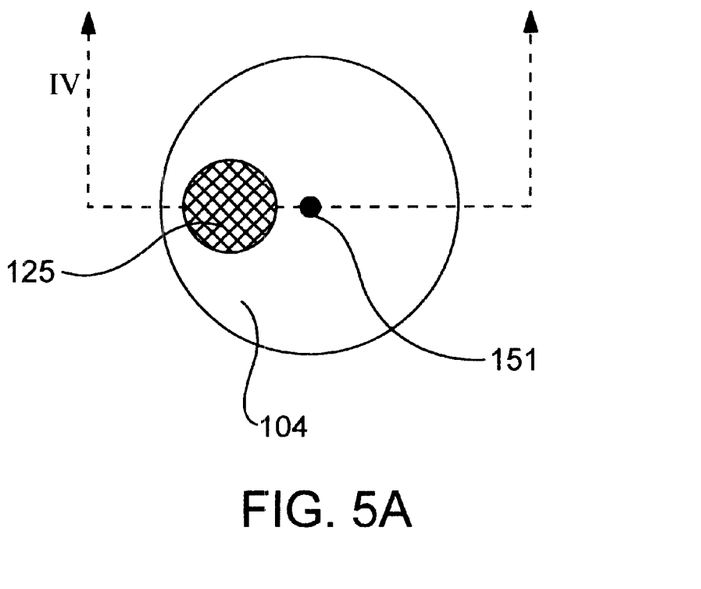
FIG. 5A shows a cross-section of a bottom view of a rotating barrel exchanger, and the placement of a longitudinal view, shown in FIG. 5B.
Figure 5B:
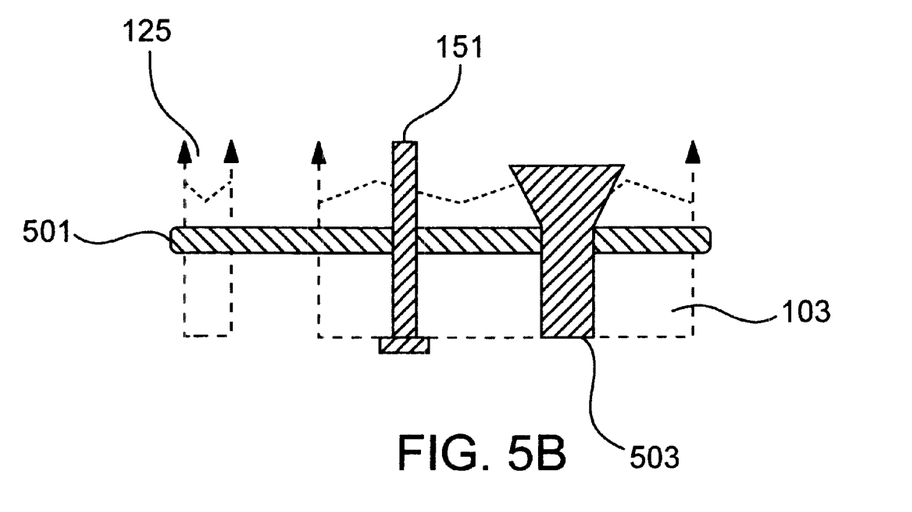

FIGS. 5A and 5B show a detailed view of a seal across the opening portal. FIG. 5A is a cross section of the closed exchanger at the base 104. The exchanger comprises a central pivot 151 and a portal 125 for movement of the expended or replacement exchangeable component. FIG. 5B is a longitudinal section of the exchanger, showing a sheet of elastomeric material 501, with a set screw 503 holding it in place. The elastomeric member forms an easily broken seal. In an alternative embodiment, the elastomeric sheet is replaced with an O ring around the portal 125. An elastomeric member Example 2

Angled Exchanger

Figure 4B:
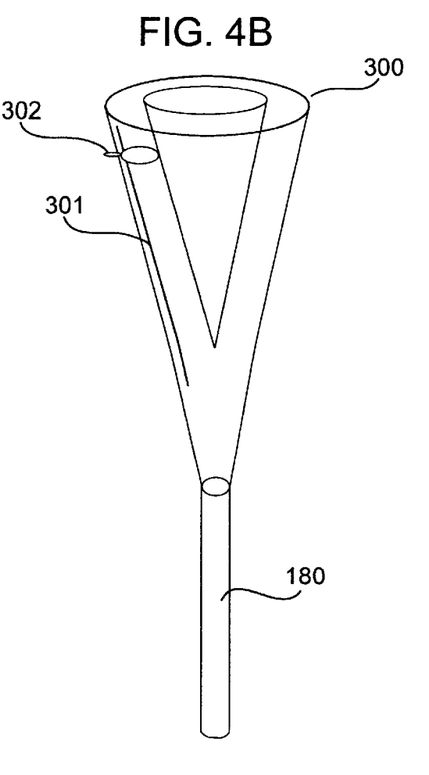

In one embodiment of the invention, the closed chamber is bifurcated into two or more compartments, each compartment capable of holding and enclosing an exchangeable component. In order to provide an access pathway through the contact element, the compartments are angled into a central point. An exchanger of this type is illustrated in FIGS. 4A and 4B.

The exchanger forms two compartments 111 and 121, into which fit the expended component and the replacement component. The compartments are held separate at the distal end (away from the contact element), but are angled toward each other at the proximal end, meeting in a opening contiguous with the contact element 180.

It will be understood by one of skill in the art that the movement elements 112 and 122 shown in Examples 1 and 2 can be used in combination with various closed chamber configurations, and in combination with different movement elements, e.g. where the withdrawal compartment and the insertion compartment have different movement-elements. In this example, a "pusher" movement element is shown for purposes of illustration.

The pusher 300 rests on top of the exchangeable component, illustrated as 110 and 120. A portion of the pusher extends outside the closed chamber, forming a handle 302. The handle fits into a channel 301 extending longitudinally down the chamber. The components are manipulated by pushing the handle and moving it up and down the channel.

Example 3

Locking mechanisms

As previously discussed, a variety of locking mechanisms may be utilized to provide a tight seal between the exchanger movement element and the exchangeable component. For example, the component and movement element may be threaded, so that the movement element screws down over the component. As shown in FIG. 6A, a small pin 601 may protrude from the exchangeable component 110, and a corresponding channel 51 be cut into the movement element 112, to form a "turn and lock" contact. In another embodiment, shown in FIG. 6B, a movable flange 52 is provided on the exchangeable component 112, which fits into a channel 602 in the movement element 112.

What is claimed is:

1. A closed exchange device comprising:
   a closed chamber capable of holding and enclosing an exchangeable component of an implantable medical device, wherein said exchangeable component comprises a depletable resource;
   a portal at a base of the closed chamber, which portal is or can be moved into a continuous open path with a contact port, said contact port and portal being of sufficient width to permit through passage of said exchangeable component; and wherein said contact port contacts the external surface of said implantable medical device so as to form a closed system;
   at least one movement element for movement of said exchangeable component through said portal, wherein said movement element is configured for withdrawing an expended component from said inplantable medical device into said closed chamber and inserting a replacement component into said implantable medical device from said closed chamber.

2. The closed exchange device of claim 1, wherein said closed chamber revolves around a central pivot, and wherein said exchangeable component can be positioned over said contact port by rotation about said pivot.

3. The closed exchange device of claim 1, wherein said movement element comprises an elongated shaft extending through said closed chamber.

4. The closed exchange device of claim 1, wherein said closed chamber is divided into at least two compartments, each compartment capable of holding and enclosing an exchangeable component.

5. The closed exchange device of claim 1, wherein said at least one movement element comprises a pusher disk comprising a handle that extends through a longitudinal channel through said closed chamber.

6. The closed exchange device of claim 1, wherein said portal is sealed with a diaphragm, which is broken by movement of said exchangeable component in or out of said closed chamber.

7. A closed exchange device comprising:
   a closed chamber capable of holding and enclosing an exchangeable component of an implantable medical device;
   a portal at the base of the closed chamber, which portal is or can be moved into a continuous open path with a contact port, said contact port and portal being of sufficient width to permit through passage of said exchangeable component; and wherein said contact port contacts the external surface of said implantable medical device so as to form a closed system;
   at least one movement element for movement of said exchangeable component through said portal, wherein said movement element comprises a locking element to secure said movement element to said exchangeable component and is configured for withdrawing an expended component from said implantable medical device into said closed chamber and inserting a replacement component Into said implantable medical device from said closed chamber.

8. The closed exchange device of claim 7, wherein said locking element comprises a screw fitting.

9. The closed exchange device of claim 7, wherein said locking element comprises a channel into which a pin can be fitted.

10. The closed exchange device of claim 7, wherein said locking element comprises a channel into which a flange can be fitted.

11. A closed exchange device comprising:
    a closed chamber capable or holding and enclosing an exchangeable components of an implantable medical device;
    a portal at a base of the closed chamber, which portal is or can be moved into a continuous open path with a contact port, said contact port and portal being of sufficient width to permit through passage of said exchangeable component; and wherein said contact port contacts the external surface of said implantable medical device so as to form a closed system;
    a replacement component for an implantable medical device; at least one movement element for movement of said exchangeable component through said portal, wherein said movement element is configured for withdrawing an expended component from said implanted medical device into said closed chamber and inserting a replacement component into said implantable medical device from said closed chamber.

12. The closed exchange device of claim 11, wherein said replacement component comprises a reservoir for holding a pharmaceutical agent.

13. A method for closed exchange of a component of an implanted medical device, the method comprising:
    contacting through a surgical incision said implanted medical device With a contact port of a closed exchange device comprising:
    a closed chamber capable of holding and enclosing an exchangeable component of an implantable medical device;
    a portal at a base of the closed chamber, which portal is or can be moved into a continuous open path with a contact port, said contact port and portal being of sufficient width to permit through passage of said exchangeable component; and wherein said contact port contacts the external surface of said implantable medical device so as to form a closed system;
    at least one movement element for movement of said exchangeable component through said portal, wherein said movement element is capable of withdrawing an expended component from said implanted medical device into said closed chamber or inserting a replacement component into said implantable medical device from said closed chamber;
    Withdrawing an expended component from said implanted medical device through said contact port, into and enclosed by said closed exchange device;
    inserting a replacement component into said implanted medical device without breaking the contact between said implanted device and said contact port.

14. The method of claim 13, wherein said closed chamber revolves around a central pivot, and wherein said exchangeable component can be positioned over said contact port by rotation about said pivot.

15. The method of claim 13, wherein said at least one movement element comprises an elongated shaft extending through said closed chamber.

16. The method of claim 13, wherein said closed chamber is divided into at least two compartments, each compartment capable of holding and enclosed an exchangeable component.

17. The method of claim 13, wherein said movement element comprises a locking element to secure said movement element to said exchangeable element.

18. The method of claim 17, wherein said locking element comprises a screw fitting.

19. The method of claim 17, wherein said locking element comprises a channel into which a pin can be fitted.

20. The method of claim 17, wherein said locking element comprises a channel into which a flange can be fitted.

21. The method of claim 17, wherein said movement element comprises a pusher disk comprising a handle that extends through a longitudinal channel through said closed chamber.

22. The method of claim 13, wherein said portal is sealed with a diaphragm, which is broken by movement of said exchangeable component in or out of said closed chamber.

23. The method of claim 13, further comprising a replacement component for an implantable medical device.

24. The method of claim 13, wherein said replacement component comprises a reservoir for holding a pharmaceutical agent.

* * * * *